United States Patent

Sugise et al.

[11] Patent Number: 5,332,844
[45] Date of Patent: Jul. 26, 1994

[54] METHOD OF PRODUCING STRAIGHT-CHAIN ACRYLONITRILE DIMERS

[75] Inventors: Ryoji Sugise; Kouichi Kashiwagi; Masashi Shirai; Toshihiro Shimakawa, all of Ube, Japan

[73] Assignee: Ube Industries, Ltd., Yamaguchi, Japan

[21] Appl. No.: 26,487

[22] Filed: Mar. 4, 1993

[30] Foreign Application Priority Data

Mar. 6, 1992 [JP] Japan .................................. 4-097512
Nov. 6, 1992 [JP] Japan .................................. 4-296972
Nov. 13, 1992 [JP] Japan .................................. 4-303912

[51] Int. Cl.$^5$ .......................................... C07C 253/30
[52] U.S. Cl. ..................................... 558/364; 558/363
[58] Field of Search ............................... 558/364, 363

[56] References Cited

U.S. PATENT DOCUMENTS

| | | | |
|---|---|---|---|
| 4,519,954 | 5/1985 | Burrington et al. | 558/364 X |
| 4,526,884 | 7/1985 | Tsou et al. | 558/364 X |
| 4,681,968 | 7/1987 | Tsou et al. | 558/364 X |

FOREIGN PATENT DOCUMENTS

| | | | |
|---|---|---|---|
| 44-24585 | 10/1969 | Japan . | |
| 45-4048 | 2/1970 | Japan . | |
| 51-1464 | 12/1976 | Japan . | |
| 54-12450 | 5/1979 | Japan . | |
| 47-6290 | 2/1992 | Japan | 558/360 |
| 47-27917 | 10/1992 | Japan | 558/364 |
| 1079696 | 8/1967 | United Kingdom | 558/364 |
| 1098726 | 1/1968 | United Kingdom . | |
| 1168958 | 10/1969 | United Kingdom | 558/364 |
| 1177059 | 1/1970 | United Kingdom | 558/364 |
| 1398089 | 6/1975 | United Kingdom . | |

OTHER PUBLICATIONS

Bulletin of the Chemical Society of Japan, Akira Misono, et al. Feb. 1968, pp. 396–401.
Derwent Publications, London 79–45161B 24 (NITT) Nitto Chem Ind KK, (MITR) Mitsubishi Rayon KK.
Derwent Publications London, 74–60788V 34 (NITT) Nitto Chem Ind Co Ltd., (MITS) Mitsubishi Rayon Co. Ltd.
Derwent Publications, London 70–11464R 08 (MITS) Mitsubishi Petrochem Co.
Derwent Publications, London 68–39172Q 00 (MITS) Mitsubishi Petro-Chem Co Ltd.

*Primary Examiner*—Joseph Paul Brust
*Attorney, Agent, or Firm*—Burgess, Ryan & Wayne

[57] ABSTRACT

Straight-chain acrylonitrile dimers including 1,4-dicyanobutene, 1,4-dicyanobutadiene and adiponitrile are produced at a high selectivity rate and yield by dimerizing acrylonitrile in the presence of a catalyst comprising at least one ruthenium compound, for example dichloro-tetrakis (dimethylsulfoxide) ruthenium, and in the presence of at least one organic acid, for example, propionic acid, and optionally in the further presence of a basic compound, a reducing compound and/or a sulfoxide compound.

25 Claims, No Drawings

METHOD OF PRODUCING STRAIGHT-CHAIN ACRYLONITRILE DIMERS

BACKGROUND OF THE INVENTION

1) Field of the Invention

The present invention relates to a method of producing straight-chain acrylonitrile dimers. More particularly, the present invention relates to a method of producing straight-chain acrylonitrile dimers including 1,4-dicyanobutene, 1,4-dicyanobutadiene and adiponitrile at a high selectivity and yield.

The above-mentioned straight-chain acrylonitrile dimers are useful as an intermediate for producing hexamethylene-diamine which is an important material for producing nylon 66, rust-inhibiting agents and vulcanization promoters for rubber materials.

2) Description of Related Art

A method of producing 1,4-dicyanobutene compounds and adiponitrile by using a catalyst comprising a ruthenium compound is well-known from A. Misono et al., Bull. Chem. Soc. Jpn., Vol. 41 No. 2, 396–401 (1968). In the method, acrylonitrile is dimerized in the presence of a ruthenium catalyst in a hydrogen gas atmosphere, Misono et al., disclose that if this method is carried out not using the hydrogen gas atmosphere, no dimerization of acrylonitrile occurs, and the dimerization of acrylonitrile can proceed only within the hydrogen gas atmosphere. This method is, however, disadvantageous in that acrylonitrile is brought into contact with the ruthenium catalyst in the hydrogen gas atmosphere, wherein dimerization of acrylonitrile proceeds and hydrogenation of acrylonitrile, which is not desired, occurs as a side reaction and a large amount of propionitrile is produced as a by-product. Therefore, to utilize the by-product consisting of propionitrile for practical use, it is necessary to return propionitrile to acrylonitrile by a dehydrogenation of propionitrile in the presence of a catalyst. However, this dehydrogenation of propionitrile exhibits a low selectivity and the dehydrogenation catalyst has poor catalytic activity. Therefore, the conversion of propionitrile to acrylonitrile is difficult and it is disadvantageous to industrialize, same.

JP-B-44-24,585, JP-B-45-4,048 and JP-B-54-12,450 disclose methods of producing straight-chain acrylonitrile dimers with an enhanced selectivity. In these methods, the selectivity of the straight-chain acrylonitrile dimers is 55 to 67%. Nevertheless, since the dimerization of acrylonitrile in these methods is carried out in the presence of hydrogen, it is unavoidable that propionitrile be produced as a by-product at a high selectivity of 33 to 45%. This by-production of propionitrile in a large amount renders the methods of the above-mentioned Japanese publication for producing straight-chain acrylonitrile dimers industrially inapplicable.

JP-B-54-12,450 discloses a method of dimerizing acrylonitrile in the presence of a catalyst and hydrogen comprising an inorganic ruthenium compound, ruthenium carboxylate, or ruthenium complex. In this method, the dimerization reaction of acrylonitrile is promoted by adding, to the reaction system, a carboxylate of a specific metal selected from lead, zinc, cadmium, tin, iron and manganese. This prior art method, is disadvantageous in that since the dimerization reaction of acrylonitrile is carried out in the presence of hydrogen, the undesirable by-production of propionitrile is unavoidable.

JP-A-51-146,420 discloses that acrylonitrile can be dimerized into dinitrile at a reaction temperature of 300° C. to 600° C. in the presence of a ruthenium catalyst in the absence of hydrogen. Nevertheless, this method is disadvantageous in that catalytic activity is unsatisfactorily low and thus when propionitrile is produced as a by-product in a low yield, the conversion of acrylonitrile to intended dimers is also poor, for example, several percent. Where acrylonitrile is converted at a high conversion rate, the by-production of propionitrile is increased, and the selectivity of $C_6$ dinitrile products is reduced. Further, the resultant dinitrile product comprises a mixture of straight-chain dimers and branched-chain dimers. Therefor, the selectivity of the intended straight-chain dimers is unsatisfactorily low.

Accordingly, there is a strong demand for the provision of a method of producing straight-chain acrylonitrile dimers while restricting the undesirable production of propionitrile that cannot be easily converted to acrylonitrile.

In the prior art methods, the use of hydrogen causes an undesirable high risk of explosion when the reaction is mixed with air or oxygen, and thus a complete sealing of the reaction system is necessary.

The above-mentioned causes the reaction procedures and apparatus to be complex and costly.

Therefore, there is a strong demand for the provision of a new method of safely producing straight-chain acrylonitrile dimers without using hydrogen.

SUMMARY OF THE INVENTION

An object of the present invention is to provide a method of producing straight-chain acrylonitrile dimers including 1,4-dicyanobutene, 1,4-dicyanobutadiene and adiponitrile at a high conversion rate, while restricting the production of propionitrile, which is an undesirable by-product.

Another object of the present invention is to provide a method of producing straight-chain acrylonitrile dimers including 1,4-dicyanobutene, 1,4-dicyanobutadiene and adiponitrile at a high selectivity and yield without using hydrogen.

The above-mentioned object can be attained by the method of the present invention for producing straight-chain acrylonitrile dimers including 1,4-dicyanobutene, 1,4-dicyanobutadiene, and adiponitrile, which comprises dimerizing acrylonitrile in the presence of a catalyst comprising at least one ruthenium compound and in the additional presence of at least one organic acid.

In the method of the present invention, the production of propionitrile as an undesirable by-product is significantly restricted.

Also, in the method of the present invention, the use of organic acid causes an β-cyanoethyl carboxylate to be produced as a by-product due to an addition reaction of the organic acid with acrylonitrile. This by-product, however, can be easily returned to the organic acid and acrylonitrile at a high selectivity in accordance with the following reaction.

$$RCOOCH_2CH_2CN \rightarrow RCOOH + CH_2=CHCN:$$

wherein R represents a hydrogen atom or a saturated or unsaturated aliphatic, and an aromatic or cycloaliphatic hydrocarbon residue, preferably having 1 to 20 carbon atoms.

Further, in the method of the present invention, since the dimerization of acrylonitrile is carried out without using hydrogen, there is no risk of an explosion occurring as a result of mixing hydrogen with air or oxygen and thus it is not necessary to completely seal the reaction system.

DESCRIPTION OF PREFERRED EMBODIMENT

As mentioned above, in the prior art methods of producing straight-chain acrylonitrile dimers, it was believed that the dimerization of acrylonitrile must be carried out in a hydrogen gas atmosphere. In such a reaction system containing a large amount of hydrogen gas, there is a high risk of explosion in a high mixing range ratio of hydrogen to air or oxygen. To avoid said explosion, the reaction system must be completely sealed from the ambient air atmosphere, which renders the dimerization procedures and apparatus complex and costly.

In the method of the present invention, hydrogen gas is not employed. Therefore, the dimerization of acrylonitrile can be carried out safely using a simple apparatus and a simple procedure.

In the dimerization of acrylonitrile in accordance with the method of the present invention, a reactor is charged with acrylonitrile, a ruthenium compound catalyst and at least one organic acid. The reaction mixture is heated to a predetermined reaction temperature and maintained at this reaction temperature for a predetermined reaction time, while agitating the reaction mixture.

In the method of the present invention, the reaction temperature is preferably from 70° C. to 220° C., more preferably from 100° C. to 180° C. When the reaction temperature is too low, the reaction rate becomes too low. Also, when the reaction temperature is too high, the catalyst is rapidly deactivated.

The reaction time is variable depending on the reaction temperature and pressure and type and the amount of catalyst. Usually, the reaction time is 0.1 to 10 hours.

There is no restriction to the reaction pressure. Usually, the reaction pressure can be controlled with in a wide range of from a reduced pressure of 50 mmHg to a high pressure of 100 kg/cm$^2$G. The dimerization of acrylonitrile in accordance with the method of the present invention can be carried out continuously by flowing acrylonitrile through the continuous reactor under a reduced pressure or intermittently in a close reactor under pressure.

In the method of the present invention, the dimerization of acrylonitrile may be carried out in a reaction medium or without using the reaction medium. Nevertheless, the reaction medium is effectively used to control the reaction rate. The reaction medium preferably comprises at least one member selected from nitrile compounds, for example, acetonitrile and propionitrile; ether compounds, for example, diethylether and diisopropylether; hydrocarbon compounds, for example, hexane and toluene; amide compounds, for example, acetamide, and N,N-dimethylacetamide; halogenated hydrocarbon compounds, for example, chloroform and carbon tetrachloride; ester compounds, for example, methyl acetate and ethyl acetate; alcohol compounds, for example, methyl alcohol and ethyl alcohol; and water.

In the method of the present invention, the ruthenium compound for the catalyst is preferably selected from the group consisting of inorganic ruthenium compounds, for example, ruthenium chloride, ruthenium bromide, ruthenium iodide, ruthenium sulfate, and ruthenium nitrate; ruthenium carboxylates, for example, ruthenium acetate, ruthenium propionate, ruthenium butanate, ruthenium pentanate, ruthenium hexanate, ruthenium stearate, ruthenium naphthenate, ruthenium oxalate, and ruthenium succinate; and ruthenium coordination compounds, for example, dichlorotetraacrylonitrile ruthenid, dichloro-tris (triphenylphosphine) ruthenium and dichloro-tetrakis (triphenylphosphine) ruthenium.

The catalyst usable for the present invention may comprise a ruthenium compound alone or a mixture of two or more ruthenium compounds.

In the method of the present invention, the ruthenium compound catalyst is preferably present in an amount of 0.0001 to 10 molar%, more preferably 0.001 to 5 molar%, based on the molar amount of acrylonitrile.

The organic acid usable for the present invention is preferably selected from carboxylic acids having 1 to 20 carbon atoms, more preferably 1 to 15 carbon atoms, for example, acetic acid, propionic acid, methylpropionic acid, dimethylpropionic acid, butanoic acid, methylbutanoic acid, ethylbutanoic acid, dimethylbutanoic acid, pentanoic acid, methylpentanoic acid, ethylpentanoic acid, dimethylpentanoic acid, trimethylpentanoic acid, hexanoic acid, methylhexanoic acid, ethylhexanoic acid, dimethylhexanoic acid, heptanoic acid, methylheptanoic acid, ethylheptanoic acid, dimethylheptanoic acid, trimethylheptanoic acid, octanoic acid, decanoic acid, dodecanoic acid, tetradecanoic acid, pentadecanoic acid, cyclohexane carboxylic acid, acrylic acid, methacrylic acid, crotonic acid, linolenic acid, linoleic acid, oleic acid, oxalic acid, succinic acid, methylsuccinic acid, glutaric acid, adipic acid, malonic acid, methylmalonic acid, dimethylmalonic acid, suberic acid, azelaic acid, sebasic acid, dodecane diacid, phthalic acid, pimelic acid, benzoic acid, methylbenzoic acid, naphthoic acid, fumaric acid, heptenoic acid, octenoic acid, hexenoic acid, cinnamic acid, lactic acid, glycolic acid, ethoxyacetic acid, methoxyacetic acid, ethoxypropionic acid and methoxypropionic acid.

Those organic acids can be employed alone or in a mixture of two or more thereof.

The organic acids added to the reaction system effectively restrict the production of propionitrile, and promote the dimerization of acrylonitrile.

Preferably, the organic acid is present in a molar amount of 0.01 to 100 times, more preferably 0.05 to 10 times the molar amount of acrylonitrile, in the reaction system.

When the organic acid is used in insufficient quantities, the resultant reaction system exhibits an undesirably reduced dimerization rate of acrylonitrile. Also, when an excessive amount of the organic acid is employed, the concentration acrylonitrile in the reaction system becomes too low, and the dimerization rate of acrylonitrile is undesirably too low.

In the method of the present invention, optionally the dimerization of acrylonitrile is carried out in the further presence of at least one member selected from basic compounds and reducing compounds. Those compounds effectively promote the dimerization of acrylonitrile.

The basic compounds are preferably selected from the group consisting of hydroxides of alkali metals, for example, sodium hydroxide, potassium hydroxide, and lithium hydroxide; carbonates of alkali metals, for example, sodium carbonate and potassium carbonate; alkali metal hydrogen carbonates, for example, hydrogen sodium carbonate; alkali metal salts of carboxylic acids, for example, sodium acetate and sodium propionate; alkoxides of alkali metals, for example, sodium methoxide and sodium ethoxide; ammonia; monoalkyl amines, for example, methyl amine and ethylamine; dialkyl amines, for example, dimethylamine and diethylamine; trialkylamines, for example, trimethylamine and triethylamine; aniline; monoalkylanilines, for example, methylaniline and ethylaniline; and dialkylaniline, for example, dimethylaniline and diethylaniline.

The basic compounds may be employed alone or in a mixture of two or more thereof. Preferably, the basic compounds are present in an amount 0.05 to 30 times, more preferably, 0.1 to 20 times the molar amount of the ruthenium compound catalyst.

The reducing compounds usable for the method of the present invention are preferably selected from organic reducing compounds, for example, organic tin compounds, organic germanium compounds, organic silicon compounds, organic boron compounds, and organic aluminum compounds; and inorganic reducing compounds, for example, hydrogenated boron compounds, hydrogenated aluminum compounds, metal-hydrogen compounds, and metal elements. The reducing compounds may be employed alone or in a mixture of two or more thereof.

Preferable reducing compounds for the present invention are trimethyl stannane, triethylstannane, tri-n-propylstannane, tri-n-butylstannane, triphenylstannane, di-n-propylstannane, di-n-butylstannane, diphenylstannane, trimethylgermane, triethylgermane, tri-n-propylgermane, sodium hydride, sodium borohydride, lithium borohydride, lithium aluminum hydride, metallic sodium, metallic magnesium and metallic zinc.

These reducing compounds may be employed alone or in a mixture of two or more thereof.

Preferably, the reducing compounds are employed in an amount 0.05 to 30 times, more preferably, 0.1 to 20 times the molar amount of the ruthenium compound catalyst.

When the basic compounds and/or the reducing compounds are employed in insufficient quantities, the resultant dimerization-promoting effect becomes too low. Also, when an excessive amount of those compounds is used, acrylonitrile in the reaction system is not effectively consumed and thus the yield of the intended acrylonitrile dimers is reduced.

In an embodiment of the method of the present invention, the dimerization of acrylonitrile is carried out in the presence of a ruthenium compound catalyst, in the additional presence of at least one organic acid and in the further presence of at least one sulfoxide compound.

The use of the sulfoxide compound in addition to the ruthenium compound catalyst and the organic acid effectively restrict the production of propionitrile and enhance the conversion of acrylonitrile to straight-chain acrylonitrile dimers.

The sulfoxide compound usable for the present invention is preferably selected from the group consisting of dimethylsulfoxide, dibutylsulfoxide, methylphenylsulfoxide, diphenylsulfoxide, dibenzylsulfoxide and tetramethylenesufloxide. Those compounds may be used alone or in a mixture of two or more thereof.

The sulfoxide compound is preferably present in a molar amount 0.01 to 100 times, more preferably, 1 to 100 times the molar amount of the ruthenium compound catalyst, in the reaction system.

When the sulfoxide compound is employed in insufficient quantities, the above-mentioned effect cannot be obtained. Also, when an excessive amount of the sulfoxide compound is used, it produces a disadvantage in that the concentration of acrylonitrile becomes too low, and the dimerization rate of acrylonitrile is undesirably reduced.

In another embodiment of the method of the present invention, the catalyst comprises dichloro-tetrakis (dimethylsulfoxide) ruthenium. When this type of catalyst is employed together with the organic acid, the production of propionitrile is significantly restricted and the conversion of acrylonitrile to the intended straight-chain acrylonitrile dimers is enhanced.

The dichloro-tetrakis (dimethylsulfoxide) ruthenium is preferably present as a catalyst in an amount of 0.001 to 10 molar%, more preferably, 0.001 to 5 molar%, based on the molar amount of acrylonitrile, in the reaction system. When the catalyst is present in insufficient amounts, the above-mentioned effect cannot be satisfactorily obtained. Also, when an excessive amount of the catalyst is used, it produces a disadvantage in that the catalyst is rapidly diactivated.

EXAMPLES

The present invention will be further illustrated by way of the following specific examples, which are only representative and in no way restrict the scope of the present invention.

EXAMPLE 1

An autoclave made from a stainless steel, having a capacity of 100 ml and equipped with a stirrer was used as a reactor. The reactor was charged with 15.0g (283 millimole) of acrylonitrile and then with 0.132g (0.38 milligram in terms of Ru atom) of ruthenium acetate and 5.0g (67.6 millimole) of propionic acid. The inside space of the reactor was filled with nitrogen gas, and the reaction mixture was heated to a temperature of 150° C. and then maintained at this temperature under a reaction pressure of 5 kg/cm$^2$G for 2 hours, to effect the dimerization of acrylonitrile.

The reactor was then cooled and the resultant reaction product mixture was subjected to a gas chromatographic analysis. It was confirmed that the reaction product mixture contained 12.0g (226 millimole) of nonreacted acrylonitrile, 1.53g (14.4 millimole) of 1,4-dicyanobutene, 0.118g (1.13 millimole) of 1,4-dicyanobutadiene, 0.061g (0.56 millimole) of adiponitrile, 0.093g (1.70 millimole) of propionitrile and 2.372g (18.7 millimole) of β-cyanoethyl propionate.

From the above-mentioned analysis results, it was found that the conversion of acrylonitrile was 20%, the total selectivity of the straight-chain acrylonitrile dimers (1,4-dicyanobutene, 1,4-dicyanobutadiene and adiponitrile) was 57%, the selectivity of propionitrile was 3%, and the selectivity of β-cyanoethyl propionate was 33%.

The above-mentioned selectivities were calculated in accordance with the following equations.

(1) Total selectivity of straight-chain acrylonitrile dimers (%)

$$= \frac{A \times 2}{B} \times 100$$

wherein A represents a total molar amount of produced 1,4-dicyanobutene, 1,4-dicyanobutadiene, and adiponitrile, and B represents a molar amount of consumed acrylonitrile.

(2) Selectivity of propionitrile (%)

$$= \frac{C}{B} \times 100$$

wherein B is as defined above, and C represents a molar amount of produced propionitrile.

(3) Selectivity of β-cyanoethyl carboxylate (%)

$$= \frac{D}{B} \times 100$$

wherein B is as defined above, D represents a molar amount of produced β-cyanoethyl carboxylate.

EXAMPLES 2 TO 8

In each of Examples 2 to 8, the same procedures as in Example 1 were carried out except that propionic acid was replaced by the carboxylic acid as indicated in Table 1.

The results are shown in Table 1.

acetate was replaced by the ruthenium compound as indicated in Table 2.

The results are shown in Table 2.

TABLE 2

| | | Item | | | |
|---|---|---|---|---|---|
| Example No. | Type of ruthenium compound | Conversion of acrylonitrile (%) | Total selectivity of straight-chain acrylonitrile dimers (%) | Selectivity of β-cyanoethyl carboxylate (%) | Selectivity of propionitrile (%) |
| 9 | Ruthenium propionate | 20 | 58 | 33 | 3 |
| 10 | Ruthenium butanate | 18 | 57 | 32 | 3 |

EXAMPLE 11

The same reactor is in Example 1 was charged with 5.0g (67.6 millimole) of propionic acid, 0.100g (0.382 milligram in terms of Ru atom) of ruthenium trichloride trihydrate, and 0,555g (1.91 millimole) of tri-n-butylstannane and then with 15.0g (283 millimole) of acrylonitrile. The resultant reaction mixture was subjected to the same dimerization procedure as in Example 1.

As a result, it was confirmed that the conversion of acrylonitrile was 20%, the total selectivity of the straight-chain acrylonitrile dimers (1,4-dicyanobutene, 1,4-dicyanobutadiene and adiponitrile) was 57%, the selectivity of propionitrile was 4% and the selectivity of β-cyanoethyl propionate was 31%.

EXAMPLES 12 TO 20

In each of Examples 12 to 20, the same procedures as in Example 11 were carried out except that tri-n-butylstannane was replaced by the reducing compound as indicated in Table 3.

The results are shown in Table 3.

TABLE 1

| | | Item | | | |
|---|---|---|---|---|---|
| Example No. | Type of carboxylic acid | Conversion of acrylonitrile (%) | Total selectivity of straight-chain acrylonitrile dimers (%) | Selectivity of β-cyanoethyl carboxylate (%) | Selectivity of propionitrile (%) |
| 2 | Acetic acid | 20 | 52 | 39 | 3 |
| 3 | Butanoic acid | 16 | 57 | 31 | 3 |
| 4 | Methylpropionic acid | 14 | 56 | 31 | 3 |
| 5 | Pentanoic acid | 14 | 56 | 30 | 3 |
| 6 | Hexanoic acid | 13 | 56 | 31 | 3 |
| 7 | Dimethyl propionic acid | 12 | 52 | 30 | 3 |
| 8 | Succinic acid | 13 | 52 | 30 | 4 |

EXAMPLES 9 AND 10

In each of Examples 9 and 10, the same procedures as in Example 1 were carried out except that ruthenium

TABLE 3

| | | Item | | | |
|---|---|---|---|---|---|
| Example No. | Type of reducing compound | Conversion of acrylonitrile (%) | Total selectivity of straight-chain acrylonitrile dimers (%) | Selectivity of β-cyanoethyl carboxylate (%) | Selectivity of propionitrile (%) |
| 12 | $HSn(CH_3)_3$ | 18 | 57 | 31 | 4 |
| 13 | $HSnEt_3$ | 18 | 57 | 30 | 4 |
| 14 | $HSn(n\text{-}pr)_3$ | 18 | 56 | 31 | 4 |
| 15 | $HSnPh_3$ | 14 | 55 | 28 | 4 |
| 16 | $H_2Sn(n\text{-}Bu)_2$ | 15 | 56 | 30 | 4 |
| 17 | $HGeEt_3$ | 18 | 57 | 31 | 4 |
| 18 | $NaBH_4$ | 18 | 55 | 29 | 4 |
| 19 | NaH | 19 | 55 | 27 | 4 |
| 20 | Metallic Na | 18 | 55 | 27 | 4 |

EXAMPLES 21 TO 23

Each of Examples 21 to 23, the same procedures as in Example 11 were carried out except that ruthenium trichloride trihydrate was replaced by the ruthenium compound as indicated in Table 4.

The results are shown in Table 4.

TABLE 4

| | | Item | | | |
|---|---|---|---|---|---|
| Example No. | Type of ruthenium compound | Conversion of acrylonitrile (%) | Total selectivity of straight-chain acrylonitrile dimers (%) | Selectivity of β-cyanoethyl carboxylate (%) | Selectivity of propionitrile (%) |
| 21 | Ruthenium acetyl acetonate | 18 | 26 | 59 | 4 |
| 22 | $RuCl_2$ (acrylonitrile)$_4$ | 20 | 58 | 33 | 3 |
| 23 | $RuCl_2(PPh_3)_3$ | 15 | 15 | 70 | 4 |

EXAMPLE 24

The same reactor as in Example 1 was charged with 5.0g (67.6 millimole) of propionic acid, 0,100g (0.382 milligram in terms of Ru atom) of ruthenium trichloride trihydrate and 0.061g (0.6 millimole) of sodium carbonate and with 15.0g (283 millimole) of acrylonitrile. The reaction mixture was subjected to the same reaction procedure as in Example 1. As a result, it was found that the conversion of acrylonitrile was 20%, the total selectivity of the straight-chain acrylonitrile dimers (1,4-dicyanobutene, 1,4-dicyanobutadiene and adiponitrile) was 57%, the selectivity of propionitrile was 3% and the selectivity of β-cyanoethyl propionate was 33%.

EXAMPLES 25 TO 28

The same procedures as in Example 24 were carried out except that sodium carbonate was replaced by the basic compound as indicated in Table 5 in an/amount equivalent to that of sodium carbonate.

The results are shown in Table 5.

EXAMPLE 31

A reactor composed of a stainless steel autoclave having a capacity of 100 ml and equipped with a stirrer was charged with 15.0g (283 millimole) of acrylonitrile and then with 0.132g (0.38 milligram in terms of ruthenium atom) of ruthenium acetate, 5.0g (67.6 millimole) of propionic acid and 0.5g (6.4 millimoles) of dimethylsulfoxide. The inside space of the autoclave was filled with nitrogen gas. The reaction mixture in the autoclave was heated up to 150° C. and then maintained at this temperature under a reaction pressure of 5 kg/cm²G for 2 hours, to dimerize acrylonitrile.

After the autoclave was cooled, the resultant reaction product mixture was subjected to a gas chromatographic analysis. It was confirmed that the reaction product mixture contained 9.15g (172 millimoles) of nonreacted acrylonitrile, 2.86g (27.0 millimole) of 1,4-dicyanobutene, 0.414g (4.0 millimole) of 1,4-dicyanobutadiene, 0.173g (1.6 millimole) of adiponitrile, 0.3g (5.5 millimole) of propionitrile and 4.37g (34.4 millimole) of β-cyanoethyl propionate.

From the analysis results, it was found that the conversion of acrylonitrile was 39%, the total selectivity of the straight-chain acrylonitrile dimers, 1,4-dicyanobutene, 1,4-dicyanobutadiene and adiponitrile) was 59%, the selectivity of propionitrile was 5%, and the selectivity of β-cyanoethyl propionate was 31%. These results are shown in Table 7.

TABLE 5

| | | Item | | | |
|---|---|---|---|---|---|
| Example No. | Type of basic compound | Conversion of acrylonitrile (%) | Total selectivity of straight-chain acrylonitrile dimers (%) | Selectivity of β-cyanoethyl carboxylate (%) | Selectivity of propionitrile (%) |
| 25 | Potassium carbonate | 20 | 57 | 33 | 3 |
| 26 | Sodium acetate | 20 | 57 | 33 | 3 |
| 27 | Sodium hydroxide | 19 | 55 | 31 | 3 |
| 28 | Triethylamine | 20 | 57 | 33 | 3 |

EXAMPLES 29 AND 30

In each of Examples 29 and 30, the same procedures as in Example 24 were carried out except that ruthenium trichloride trihydrate was replaced by the ruthenium compound as indicated in Table 6.

The results are shown in Table 6.

EXAMPLES 32 TO 35

In each of Examples 32 to 35, the same procedures as in Example 31 were carried out except that propionic acid was replaced by the carboxylic acid as indicated in Table 7.

The results are shown in Table 7.

TABLE 6

| | | Item | | | |
|---|---|---|---|---|---|
| Example No. | Type of ruthenium compound | Conversion of acrylonitrile (%) | Total selectivity of straight-chain acrylonitrile dimers (%) | Selectivity of β-cyanoethyl carboxylate (%) | Selectivity of propionitrile (%) |
| 29 | Ruthenium acetyl acetonate | 10 | 15 | 70 | 3 |
| 30 | $RuCl_2$ (acrylonitrile)$_4$ | 18 | 58 | 33 | 3 |

TABLE 7

| Example No. | Type of carboxylic acid | Conversion of acrylonitrile (%) | Total selectivity of straight-chain acrylonitrile dimers (%) | Selectivity of propionitrile (%) | Selectivity of β-cyanoethyl carboxylate (%) |
|---|---|---|---|---|---|
| 31 | Propionic acid | 39 | 59 | 5 | 31 |
| 32 | Acetic acid | 39 | 58 | 5 | 32 |
| 33 | Butanoic acid | 35 | 57 | 5 | 30 |
| 34 | Pentanoic acid | 32 | 56 | 5 | 30 |
| 35 | Hexanoic acid | 30 | 56 | 4 | 30 |

EXAMPLE 36

A reactor composed of a stainless steel autoclave having a capacity of 100 ml and equipped with a stirrer was charged with 15.0g (283 millimole) of acrylonitrile and then with 0.1g (0.38 milligram in terms of ruthenium atom) of ruthenium trichloride trihydrate, 0.08g (0.76 millimole) of sodium carbonate, 5.0g 67.6 millimole) of propionic acid and 0.5g (6.4 millimoles) of dimethylsulfoxide. The inside space of the autoclave was filled with nitrogen gas. The reaction mixture in the autoclave was heated to 150° C. and then maintained at this temperature under a reaction pressure of 5 kg/cm²G for 2 hours, to dimerize acrylonitrile.

After the autoclave was cooled, the resultant reaction product mixture was subjected to the same gas chromatographic analysis as in Example 31.

From the analysis results, it was found that the conversion of acrylonitrile was 39%, the total selectivity of the straight-chain acrylonitrile dimers (1,4-dicyanobutene, 1,4-dicyanobutadiene and adiponitrile) was 59%, the selectivity of propionitrile was 5%, and the selectivity of β-cyanoethyl propionate was 31%. These results are shown in Table 8.

EXAMPLES 37 TO 42

In each of Examples 37 to 42, the same procedures as in Example 36 were carried out except that sodium carbonate was replaced by the basic compound or the reducing compound as indicated in Table 8, in an amount equivalent to that of sodium carbonate used in Example 36.

The results are shown in Table 8.

TABLE 8

| Example No. | Type of basic compound or reducing compound | Conversion of acrylonitrile (%) | Total selectivity of straight-chain acrylonitrile dimers (%) | Selectivity of propionitrile (%) | Selectivity of β-cyanoethyl carboxylate (%) |
|---|---|---|---|---|---|
| 36 | Sodium carbonate | 39 | 59 | 5 | 31 |
| 37 | Sodium acetate | 39 | 58 | 5 | 32 |
| 38 | Sodium propionate | 39 | 59 | 5 | 31 |
| 39 | Potassium carbonate | 39 | ·58 | 5 | 32 |
| 40 | Sodium hydroxide | 34 | 57 | 5 | 30 |
| 41 | Triethylamine | 32 | 57 | 4 | 30 |
| 42 | Tributyl stannane | 35 | 57 | 5 | 30 |

EXAMPLES 43 TO 47

In each of Examples 43 to 47, the same procedures as in Example 31 were carried out except that dimethylsulfoxide was replaced by the sulfoxide compound as indicated in Table 9.

The analysis results are shown in Table 9.

TABLE 9

| Example No. | Type of sulfoxide compound | Conversion of acrylonitrile (%) | Total selectivity of straight-chain acrylonitrile dimers (%) | Selectivity of propionitrile (%) | Selectivity of β-cyanoethyl carboxylate (%) |
|---|---|---|---|---|---|
| 43 | Dibutylsulfoxide | 28 | 54 | 4 | 32 |
| 44 | Methylphenylsulfoxide | 31 | 55 | 3 | 32 |
| 45 | Diphenylsulfoxide | 29 | 59 | 3 | 27 |
| 46 | Dibenzylsulfoxide | 22 | 55 | 5 | 30 |
| 47 | Tetramethylene sulfoxide | 37 | 58 | 5 | 30 |

EXAMPLE 48

A reactor composed of a stainless steel autoclave having a capacity of 500 ml and equipped with a stirrer was charged with 75.0g (1.41 mole) of acrylonitrile and then with 0.68g (1.40 millimole) of dichloro-tetrakis (dimethyl-sulfoxide) ruthenium, 0,185g (1.75 millimole) of sodium carbonate and 25g (0,337 mole) of propionic acid.

The inside space of the autoclave was filled with nitrogen gas. The reaction mixture in the autoclave was heated to 150° C. and then maintained at this temperature under a reaction pressure of 5 kg/cm²G for 2 hours, to dimerize acrylonitrile.

After the autoclave was cooled, the resultant reaction product mixture was subjected to a gas chromatographic analysis.

From the analysis results, it was found that the conversion of acrylonitrile was 29%, the total selectivity of the straight-chain acrylonitrile dimers (1,4-dicyanobutene, 1,4-dicyanobutadiene and adiponitrile) was 59%, the selectivity of propionitrile was 3%, and the selectivity of β-cyanoethyl propionate was 34%.

EXAMPLES 49 TO 52

In each of Examples 49 to 52, the same procedures as in Example 48 were carried out except that propionic acid was replaced by the carboxylic acid as indicated in Table 10.

The results are shown in Table 10.

TABLE 10

| | | Item | | |
|---|---|---|---|---|
| Example No. | Type of carboxylix acid | Conversion of acrylonitrile (%) | Total selectivity of straight-chain acrylonitrile dimers (%) | Selectivity of propionitrile (%) | Selectivity of β-cyanoethyl carboxylate (%) |
| 49 | Acetic acid | 29 | 57 | 3 | 32 |
| 50 | Butanoic acid | 25 | 57 | 3 | 32 |
| 51 | Pentanoic acid | 22 | 56 | 3 | 32 |
| 52 | Hexanoic acid | 20 | 56 | 3 | 32 |

EXAMPLES 53 TO 58

In each of Examples 53 to 58, the same procedures as in Example 48 were carried out except that sodium carbonate was replaced by the basic compound or the reducing compound as indicated in Table 11 in the same amount as that of sodium carbonate used in Example 48.

The analysis results are as shown in Table 11.

TABLE 11

| | | Item | | |
|---|---|---|---|---|
| Example No. | Type of basic compound or reducing compound | Conversion of acrylonitrile (%) | Total selectivity of straight-chain acrylonitrile dimers (%) | Selectivity of propionitrile (%) | Selectivity of β-cyanoethyl carboxylate (%) |
| 53 | Sodium acetate | 29 | 58 | 3 | 32 |
| 54 | Potassium carbonate | 29 | 58 | 3 | 32 |
| 55 | Sodium hydroxide | 24 | 57 | 3 | 32 |
| 56 | Triethylamine | 22 | 57 | 3 | 32 |
| 57 | Tributylstannate | 25 | 57 | 3 | 32 |
| 58 | Silver acetate | 29 | 57 | 3 | 32 |

As clearly indicated in Tables 1 to 11, the method of the present invention effectively dimerizes acrylonitrile to provide straight-chain acrylonitrile dimers at a relatively high conversion rate, while restricting the formation of undesirable propionitrile, which is difficult to convert to acrylonitrile. In the method of the present invention, β-cyanoalkyl carboxylate is produced as a by-product. This compound, however, can be easily returned to acrylonitrile and a carboxylic acid, which can be utilized for the method of the present invention. Accordingly, in the method of the present invention, acrylonitrile can be reacted at an enhanced conversion, and the resultant straight-chain acrylonitrile dimers can be obtained at a high total selectivity rate.

We claim:

1. A method of producing straight-chain acrylonitrile dimers including 1,4-dicyanobutene, 1,4-dicyanobutadiene and adiponitrile, comprising dimerizing acrylonitrile in the presence of a catalyst consisting essentially of at least one ruthenium compound selected from the group consisting of inorganic ruthenium compounds, ruthenium carboxylates and ruthenium coordination compounds and in the additional presence of an organic carboxylic acid having 1 to 20 atoms.

2. The method as claimed in claim 1, the dimerizing step is carried out in the absence of hydrogen gas.

3. The method as claimed in claim 1, wherein the dimerizing step is carried out at a temperature of 70° to 220° C.

4. The method as claimed in claim 1, wherein the dimerizing step is carried out under a pressure of from 50 mmHg to 100 kg/cm$^2$G.

5. The method as claimed in claim 1, wherein the ruthenium compound for the catalyst is selected from the group consisting of ruthenium chloride, ruthenium bromide, ruthenium iodide, ruthenium sulfate, ruthenium nitrate, ruthenium acetate, ruthenium propionate, ruthenium butanate, ruthenium pentanate, ruthenium hexanate, ruthenium stearate, ruthenium naphthenate, ruthenium oxalate, ruthenium succinate, dichlorotetraacrylonitrile ruthenium, dichloro-tris (triphenylphosphine) ruthenium, dichlorotetrakis(triphenylphosphine) ruthenium.

6. The method as claimed in claim 1, wherein the catalyst is present in an amount of 0.001 to 10 molar% based on the molar amount of acrylonitrile.

7. The method as claimed in claim 1, wherein the organic carboxylic acid is selected from the group consisting of acetic acid, propionic acid, methylpropionic acid, dimethylpropionic acid, butanoic acid, methylbutanoic acid, ethylbutanoic acid, dimethylbutanoic acid, pentanoic acid, methylpentanoic acid, ethylpentanoic acid, dimethylpentanoic acid, trimethylpentanoic acid, hexanoic acid, methylhexanoic acid, ethylhexanoic acid, dimethylhexanoic acid, heptanoic acid, methylheptanoic acid, ethylheptanoic acid, dimethylheptanoic acid, trimethylheptanoic acid, octanoic acid, decanoic acid, dodecanoic acid, tetradecanoic acid, pentadecanoic acid, cyclohexane carboxylic acid, acrylic acid, methacrylic acid, crotonic acid, linolenic acid, linoleic acid, oleic acid, oxalic acid, succinic acid, methylsuccinic acid, glutaric acid, adipic acid, malonic acid, methylmalonic acid, dimethylmalonic acid, suberic acid, azelaic acid, sebacic acid, dodecane diacid, phthalic acid, pimelic acid, benzoic acid, methylbenzoic acid, naphthoic acid, fumaric acid, heptenoic acid, octenoic acid, hexenoic acid, cinnamic acid, lactic acid, glycolic acid ethoxyacetic acid, methoxyacetic acid, ethoxypropionic acid and methoxypropionic acid.

8. The method as claimed in claim 1, wherein the organic acid is present in a molar amount of 0.01 to 100 times the molar amount of acrylonitrile.

9. The method as claimed in claim 1, wherein the dimerizing step is carried out in the further presence of a basic compound.

10. The method as claimed in claim 9, wherein the basic compound is selected from the group consisting of hydroxides of alkali metals, carbonates of alkali metals, hydrogen alkali metal carbonates, alkali metal salts of carboxylic acids, alkoxides of alkali metals, ammonia, monoalkyl amines, dialkyl amines trialkyl amines, aniline, monoalkylanilines and dialkylanilines.

11. The method as claimed in claim 9, wherein the basic compound is present in a molar amount of 0.05 to 30 times the molar amount of the ruthenium compound catalyst.

12. The method as claimed in claim 1, wherein the dimerizing step is carried out in the further presence of at least one sulfoxide compound.

13. The method as claimed in claim 12, wherein the sulfoxide compound is selected from the group consisting of dimethylsulfoxide, dibutylsulfoxide, methylphenylsulfoxide, diphenylsulfoxide, dibenzylsulfoxide and tetramethylenesulfoxide.

14. The method as claimed in claim 12, wherein the sulfoxide compound is present in a molar amount of 0.01 to 100 times the molar amount of the ruthenium compound catalyst.

15. The method as claimed in claim 1, wherein the catalyst comprises dichloro-tetrakis (dimethylsulfoxide) ruthenium.

16. The method as claimed in claim 15, wherein the dichloro-tetrakis (dimethylsulfoxide) ruthenium is present in an amount of 0.001 to 10 molar% based on the molar amount of acrylonitrile.

17. The method as claimed in claim 1, wherein the dimerizing step is carried out without using a reaction medium.

18. The method as claimed in claim 1, wherein the dimerizing step is carried out in a reaction medium.

19. The method as claimed in claim 1, wherein the inorganic ruthenium compound for catalyst is selected from the group consisting of ruthenium chloride, ruthenium bromide, ruthenium iodide, ruthenium trichloride trihydrate, ruthenium sulfate and ruthenium nitrate.

20. The method as claimed in claim 1, wherein the ruthenium carboxylate for catalyst is selected from the group consisting of ruthenium acetate, ruthenium propionate, ruthenium butanate, ruthenium pentanate, ruthenium hexanate, ruthenium stearate, ruthenium naphthenate, ruthenium oxalate and ruthenium succinate.

21. The method as claimed in claim 1, wherein the ruthenium coordination compound for catalyst is selected from the group consisting of dichloro-tetra-acrylonitrile ruthenium, ruthenium acetyl-acetonate, dichloro-tris (triphenylphosphine) ruthenium, dichloro-tetra-kis(triphenylphosphine) ruthenium and dichloro-tetra-kis(dimethyl-sulfoxide) ruthenium.

22. The method as claimed in claim 1, wherein the dimerizing step is carried out in the further presence of a reducing agent.

23. The method as claimed in claim 22, wherein the reducing agent is selected from the group consisting of trimethylstannane, triethylstannane, tri-n-propylstannane, tri-n-butylstannane, triphenylstannane, di-n-propylstannane, di-n-butylstannane, diphenylstannane, trimethylgermane, triethylgermane, tri-n-propylgermane, sodium hydride, sodium borohydride, lithium borohydride, lithium aluminum hydride, metallic sodium, methallic magnesium, metallic zinc and silver acetate.

24. The method as claimed in claim 18, wherein the reaction medium consists of at least one member selected from the group consisting of nitrile compounds, ether compounds, hydrocarbon compounds, amide compounds, halogenated hydrocarbon compounds, ester compounds, alcohol compounds and water.

25. The method as claimed in claim 22, wherein the reducing compound is present in a molar amount of 0.05 to 30 times the molar amount of the ruthenium compound catalyst.

* * * * *